(12) United States Patent
Jon et al.

(10) Patent No.: US 11,571,486 B2
(45) Date of Patent: Feb. 7, 2023

(54) BILIRUBIN DERIVATIVE-BASED DIAGNOSTIC AND THERAPEUTIC ULTRASOUND CONTRAST AGENT

(71) Applicant: Bilix Co., Ltd., Seoul (KR)

(72) Inventors: Sang Yong Jon, Daejeon (KR); Dong Yun Lee, Daejeon (KR); Yong Hyun Lee, Daejeon (KR); Jin Yong Kim, Daejeon (KR)

(73) Assignee: Bilix Co., Ltd., Seoul (KR)

( * ) Notice: Subject to any disclaimer, the term of this patent is extended or adjusted under 35 U.S.C. 154(b) by 99 days.

(21) Appl. No.: 16/985,219

(22) Filed: Aug. 4, 2020

(65) Prior Publication Data

US 2021/0030897 A1    Feb. 4, 2021

Related U.S. Application Data

(63) Continuation of application No. PCT/KR2019/001443, filed on Feb. 1, 2019.

(30) Foreign Application Priority Data

Feb. 5, 2018  (KR) .......................... 10-2018-0014160

(51) Int. Cl.

| | |
|---|---|
| *A61K 9/50* | (2006.01) |
| *A61K 31/136* | (2006.01) |
| *A61K 49/18* | (2006.01) |
| *A61K 33/243* | (2019.01) |
| *A61K 31/282* | (2006.01) |
| *A61K 31/337* | (2006.01) |
| *A61K 31/704* | (2006.01) |
| *A61K 31/7068* | (2006.01) |
| *A61K 49/22* | (2006.01) |

(52) U.S. Cl.
CPC .......... *A61K 49/186* (2013.01); *A61K 9/5031* (2013.01); *A61K 31/136* (2013.01); *A61K 31/282* (2013.01); *A61K 31/337* (2013.01); *A61K 31/704* (2013.01); *A61K 31/7068* (2013.01); *A61K 33/243* (2019.01); *A61K 49/221* (2013.01); *A61K 49/223* (2013.01)

(58) Field of Classification Search
CPC ....... A61K 9/50; A61K 31/136; A61K 49/223
See application file for complete search history.

(56) References Cited

U.S. PATENT DOCUMENTS

| | | | |
|---|---|---|---|
| 2008/0070791 A1* | 3/2008 | Morag | .................... C07K 14/33 506/17 |
| 2008/0070971 A1 | 3/2008 | Wang | |
| 2017/0028076 A1* | 2/2017 | Jon | ...................... A61K 31/704 |

FOREIGN PATENT DOCUMENTS

| | | |
|---|---|---|
| CN | 103212094 A | 7/2013 |
| EP | 3 622 969 A2 | 3/2020 |
| JP | H07-173079 A | 7/1995 |
| JP | 2010-280678 A | 12/2010 |
| KR | 10-2015-0079436 A | 7/2015 |
| KR | 10-2017-0085278 A | 7/2017 |
| WO | WO 99/55383 A2 | 11/1999 |
| WO | WO 2014/163221 A1 | 10/2014 |
| WO | WO 2016/199430 A1 | 12/2016 |

OTHER PUBLICATIONS

Chengcheng Niu et al., Ddoxorubicin loaded superparamagnetic PLGA0iron oxide multifunctional microbubbles for dual-mode US/MR imaging and therapy of metastasis in lymph nodes, Biomaterials, 34, 2307-2317. (Year: 2013).*
European Search Report For EP19747609.6 dated Oct. 26, 2021 from European patent office in a counterpart European patent application.
International Search Report for PCT/KR2019/001443 dated May 13, 2019.
Yonghyun Lee et al "Bilirubin Nanoparticles as a Nanomedicine for Anti-inflammation Therapy", Angewandte Chemie International Edition, vol. 55, No. 26, May 4, 2016 (May 4, 2016), pp. 7460-7463, XP055317213, DE ISSN: 1433-7851, DOI: 10.1002/anie. 201602525.
E Stride et al "Microbubble ultrasound contrast agents: A review", Proceedings of the Institution of Mechanical Engineers.Journal of Engineering in Medicine. Part H, Mechanical Engineering Publications Ltd, London, GB, vol. 217, No. H6, Nov. 1, 2003 (Nov. 1, 2003), pp. 429-447, XP008078024, ISSN: 0954-4119, DOI: 10.1243/09544110360729072.
Jeong Yu Lee et al., "Nanoparticle-Loaded Protein-Polymer Nanodroplets for Improved Stability and Conversion Efficiency in Ultrasound Imaging and Drug Delivery", Advanced Materials, 2015, vol. 27, Nr:37, pp. 5484-5492, DOI: http://dx.doi.org/10.1002/adma.201502022.
Lee, Dong Yun et al., "Black Pigment Gallstone Inspired Platinum-Chelated Bilirubin Nanoparticles for Combined Photoacoustic Imaging and Photothermal Therapy of Cancers", Angewandte Chemie International Edition, 2017, vol. 56, Nr:44, pp. 13684-13688 (English abstract is submitted herewith.).
Elizabeth Huynh et al "Porphysome nanotechnology: A paradigm shift in lipid-based supramolecular structures", Nano Today (2014) 9, 212-222.
Office action dated Nov. 8, 2022 from Japan Intellectual Property Office in a counterpart Japanese Patent Application No. 2020-542067 (English translation is also submitted herewith.).

* cited by examiner

*Primary Examiner* — Michael G. Hartley
*Assistant Examiner* — Jagadishwar R Samala
(74) *Attorney, Agent, or Firm* — The PL Law Group, PLLC

(57) ABSTRACT

Provided is a bilirubin derivative-based ultrasound contrast agent for diagnosis and treatment. The fine particles including the bilirubin derivative are sensitive to reactive oxygen species (ROS), bind with hydrophobic drugs, and can effectively chelate metals such as iron oxide nanoparticles. Therefore, the fine particle of the present invention can be used as an ultrasound contrast agent for diagnosis, as a magnetic resonance imaging contrast agent, or as a carrier for hydrophobic drugs or platinum-based drugs.

10 Claims, 10 Drawing Sheets

BILIRUBIN DERIVATIVE-BASED DIAGNOSTIC AND THERAPEUTIC ULTRASOUND CONTRAST AGENT

This application is a continuation application of International Application No. PCT/KR2019/001443 filed on Feb. 1, 2019, which claims the benefit of and priority to Korean Patent Application No. 10-2018-0014160 filed with the Korean Intellectual Property Office on Feb. 5, 2018, which are herein incorporated by reference in their entirety.

TECHNICAL FIELD

The present invention relates to a bilirubin derivative-based ultrasound contrast agent for diagnosis and treatment.

BACKGROUND OF INVENTION

Ultrasound refers to sound waves with frequency higher than 20,000 Hz, which is outside the human hearing range. Ultrasonic waves are spread, reflected, absorbed, and dispersed at various interfaces such as internal organs, bones, muscle tissues, and blood. Imaging technique using the difference in signal between interfaces is known as ultrasonography.

An ultrasound imaging device is one of the most widely used medical diagnostic technologies, with its excellent mobility and accessibility. An ultrasound imaging device is the safest and fastest diagnostic technique compared to techniques such as magnetic resonance imaging (MRI) and computed tomography (CT). It is a low-cost, high-efficiency diagnostic technique. However, since the image quality is low compared to techniques such as MRI, CT, and PET, various ultrasound contrast agents have been developed to improve the image quality.

An ultrasound contrast agent is a form of microbubble or nanobubble including a hydrophobic gas core, located at the center, surrounded by a shell of proteins, (phospho)lipids, or polymers. When the gaseous bubble of the ultrasound contrast agent enters the bloodstream, which is an aqueous environment, and is exposed to ultrasound, resonance and ultrasound dispersion occurs. This increases the image signal, and a clearer image can be obtained.

However, in order to enhance the image at a desired location, the contrast agent bubbles must not burst due to temperature or pressure changes at the interface between the gas and the liquid. Therefore, the substances constituting the shell, which surrounds the ultrasound contrast agent, must impart structural stability to the bubbles and be little influenced by the body's immune system.

Hydrophobic molecules have mainly been studied as candidate substances that make contact with the core of the ultrasound contrast agent. Recent studies have branched beyond diagnosis using ultrasound, and have been attempting to non-invasively treat diseases using ultrasound. In particular, high-intensity focused ultrasound (HIFU) that uses non-ionizing ultrasonic waves to generate heat in a focused area of tissues has been used to burn the tissue area (thermal ablation). Further, ultrasound contrast agents that simultaneously perform diagnosis and treatment have emerged as a new modality.

PRIOR ART REFERENCES

[Patent Documents] Korean Patent No. 10-1681299

DETAILED DESCRIPTION OF THE INVENTION

Problems to be Solved

The present inventors made extensive efforts to develop new ultrasound contrast agent particles that can simultaneously perform diagnosis and treatment using ultrasound. Over the course of the study, the inventors found that an amphiphilic bilirubin derivative, prepared by introducing a hydrophilic molecule into bilirubin, can be used to form a shell of the ultrasound contrast agent particles with a hydrophobic gas core. It was further confirmed that the bilirubin derivative shell reacts sensitively to reactive oxygen species (ROS), and furthermore, can effectively load or chelate such metals as iron oxide nanoparticles. The present invention has been completed with such confirmations.

Accordingly, an objective of the present invention is to provide a fine particle including a core containing a gas; and a shell comprising a bilirubin derivative and surrounding the core.

Another objective of the present invention is to provide an ultrasound contrast agent containing the fine particle.

Still another objective of the present invention is to provide a method of obtaining a diagnostic image of a patient, including: administrating an effective amount of the ultrasound contrast agent which contains the fine particle, to a patient, and imaging a body part or a tissue of the patient.

Still another objective of the present invention is to provide a method of obtaining a diagnostic image of a patient, including: administrating an effective amount of an ultrasound contrast agent which contains the fine particle, to a patient, and treating a lesion of a body part or a tissue of the patient.

Still another objective of the present invention is to provide a method for preparing the fine particle mentioned above.

SUMMARY OF INVENTION

According to an aspect of the present invention, the present invention provides a fine particle, including: a core containing a gas; and a shell comprising a bilirubin derivative and surrounding the core. The fine particle of the present invention has a bubble (foam) structure including the core and the shell surrounding a surface of the core.

The core contains the hydrophobic gas therein. Therefore, the fine particle of the present invention is synonymous with "fine foam" or "fine bubble". In addition, the "fine particle" of the present invention has a particle size of 1 nm-100 μm. Therefore, the term "fine particle" can be interchangeable with the terms "nanobubble" or "microbubble".

In addition, the fine particle of the present invention can be used as a contrast agent that can enhance the signal of the ultrasound image. The ultrasound contrast agent is used for diagnosis using the difference in ultrasound signal generated at the nano- or micro-sized bubble interface. The nano- or micro-sized bubble is administered into a body. Ultrasonic contrast agents generally have a structure in which a gas core is wrapped by a thin film (shell) made of proteins, lipids, or polymers.

Due to the intrinsic properties of gaseous molecules, the gas core of the contrast agent is sensitive to changes in surface tension and external pressure. Therefore, the ultrasound contrast agent in a liquid form has a lower stability in the blood than the ultrasound contrast agent in a solid form.

In order for the ultrasound contrast agent to maintain a stable state in the blood, its gas core must be a hydrophobic gas which has a low solubility in the blood. In addition, the substance constituting the shell of the contrast agent should impart structural stability so that the bubble does not burst due to a change in temperature or pressure at the interface between the gas and the liquid, and is little influenced by the body's immune system.

The present invention employs the bilirubin derivatives as a substance constituting the shell of the above-mentioned fine particle. In other words, the fine particle of the present invention uses a bilirubin derivative as a material forming a shell. The hydrophobic gas of the fine particle of the present invention can be any conventional hydrophobic gas.

According to an embodiment of the invention, the hydrophobic gas is, for example, air, nitrogen, helium, argon, carbon dioxide, sulfur hexafluoride ($SF_6$) and $C_1$ to $C_{10}$ perfluorocarbons. However, the hydrophobic gas is not limited thereto. Examples of $C_1$ to $C_{10}$ perfluorocarbons include perfluorobutane, perfluoropentane, octafluoropropane, and decafluoropentane.

According to an embodiment of the present invention, the bilirubin derivative is a hydrophilic molecule covalently bonded to bilirubin. In the bilirubin derivative, hydrophobic bilirubins and hydrophilic molecules are covalently bound to have amphiphilic properties.

As used herein, the term "hydrophilicity" refers to the tendency of polar substances which have strong affinity for water and high solubility in water. For example, a hydrophilic polymer compound is highly soluble in water. When water droplets are dropped on a solid surface coated with a hydrophilic material, the contact angle is equal to or less than 90°.

As used herein, the term "hydrophobicity" refers to the tendency of nonpolar substances to be excluded from water molecules and aggregate. When the hydrophobic substance is in the hydrophilic liquid, the hydrophobic interaction between the hydrophobic substances increases and thereby the hydrophobic substances aggregate. When water droplets are dropped on a solid surface coated with a hydrophobic polymer compound, the contact angle is 90° or more.

According to a specific embodiment of the present invention, the hydrophilic molecule (compound) can be dextran, carbodextran, polysaccharide, cyclodextran, pluronic, cellulose, starch, glycogen, carbohydrate, monosaccharide, disaccharide and oligosaccharide, peptide, polyphosphazene, polylactide, poly(lactic-co-glycolic acid), polycaprolactone, polyanhydride, polymaleic acid and derivatives of polymalic acid, poly alkyl cyanoacrylate, polyhydroxybutyrate, polycarbonate, polyorthoester, polyethylene glycol (PEG), methoxy polyethylene glycol (methoxy polyethylene glycol, mPEG), polypropylene glycol, polyethylenimine, poly-L-lysine, polyglycolide, polymethyl methacrylate, Polyvinylpyrrolidone, poly(acrylate), poly(acrylamide), poly(vinylester), poly(vinyl alcohol) (poly(vinyl alcohol)), polystyrene, polyoxide, polyelectrolyte, poly(1-nitropropylene), poly(N-vinylpyrrolidone), poly(N-vinyl pyrrolidone), polyvinylamine, poly(beta-hydroxyethyl methacrylate), polyethylene oxide, poly(ethylene oxide-b-propylene oxide), polylysine, a combination thereof, or any hydrophilic molecule that can be used in the art.

The hydrophilic molecule of the present invention is covalently bound to the carboxyl group of bilirubin to form a hydrophilic/amphiphilic bilirubin derivative. See Amphiphiles: Molecular Assembly and Applications (ACS Symposium Series) 1st Edition by Ramanathan Nagarajan and Various Self-Assembly Behaviors of Amphiphilic Molecules in Ionic Liquids By Bin Dong and Yanan Gao, DOI:10.5772/59095.

Bilirubin, to which hydrophilic molecules are covalently bound, has amphiphilic properties. Therefore, it is not only soluble in a water-soluble solvent, but also spontaneously self-assembled to form particles, and thus can be applied to both hydrophobic and hydrophilic agents.

As shown in the examples of the present invention, the present inventors prepared a carboxylate PEGylated bilirubin (PEG-BR, Pegylated bilirubin) through a simple amide bond synthesis from a hydrophilic compound polyethylene glycol (polyethylene glycol, PEG). According to an embodiment of the invention, the hydrophilic molecule (compound) is polyethylene glycol or a derivative thereof.

The polyethylene glycol derivatives include, for example, methoxy polyethylene glycol (PEG), succinimide of PEG propionic acid (succinimide of PEG propionic acid), succinimide of PEG butanoic acid (succinimide of PEG butanoic acid), branched PEG-HNS, PEG succinimidyl succinate, carboxymethylated carboxymethylated PEG, PEG benzotriazole carbonate of PEG, PEG-glycidyl ether, PEG-oxycarbonylimidazole, PEG nitrophenyl carbonates, PEG-aldehyde, PEG succinimidyl carboxymethyl ester, and PEG succinimidyl ester.

According to an embodiment of the present invention, the average molecular weight of the polyethylene glycol is 200 to 20000 Da. According to another embodiment, a hydrophilic molecule that can be used in the present invention is a peptide composed of two or more (e.g. 2-50) amino acids. The amino acids include not only L-amino acids, but also unnatural amino acids and derivatives.

Hydrophilic amino acids include glutamine, aspartic acid, glutamic acid, threonine, asparagine, arginine, serine, and hydrophobic amino acids include phenylalanine, tryptophan, isoleucine, leucine, proline, methionine, valine, and alanine. Non-coding hydrophilic amino acids include, for example, Cit and hCys.

Those skilled in the art can easily synthesize a hydrophilic polypeptide based on the above information and a peptide synthesis technique well-known in the art and use the peptide in preparing the bilirubin nanoparticles.

The hydrophilic molecule includes not only the compounds mentioned above, but also derivatives thereof. More specifically, the hydrophilic molecules may have an amine group or be modified to have an amine group. In this case, it is apparent to those skilled in the art that the carboxyl group of bilirubin can be easily covalently bonded to the amine group of the hydrophilic molecule through an amide bond.

According to another embodiment of the present invention, the fine particle of the present invention further comprises a metal ion or a metal compound selected from the group consisting of Cu, Ga, Rb, Zr, Y, Tc, In, Ti, Gd, Mn, Fe, Au, Pt, Zn, Na, K, Mg, Ca, Sr, and lanthanide metals.

According to another embodiment of the present invention, the fine particle of the present invention may further include a platinum-based anti-cancer drug selected from the group consisting of cisplatin, carboplatin, oxaliplatin, nedaplatin, and heptaplatin groups.

According to another embodiment of the present invention, the fine particle of the present invention may further include superparamagnetic iron oxide nanoparticle (SPION).

As shown in embodiments of the present invention, the fine particle (microbubbles) of the present invention can efficiently load iron oxide nanoparticle (SPION), and can be easily extracted using a magnet. The metal ions, the metal compounds, the platinum-based anti-cancer drugs, the superparamagnetic iron oxide nanoparticles, and the like, which are additionally included in the fine particle of the present invention, each impart additional functionality to the fine particle serving as an ultrasound contrast agent.

Another objective of the present invention is to provide an ultrasound contrast agent including the fine particle of the present invention described above. According to the present invention, the ultrasound contrast agent can be applied in all ultrasound examinations used in the conventional art. This includes abdominal ultrasound, genitourinary ultrasound, breast ultrasound, musculoskeletal ultrasound, thyroid ultrasound, cardiac ultrasound, transcranial ultrasound, intravascular ultrasound (IVUS), and Doppler sonography. In addition, it is applicable to all diagnostic procedures such as Endoscopic Ultrasound (EUS) and Endo-Bronchial Ultrasound (EBUS).

Particularly, the fine particle including iron oxide nanoparticle (SPION) according to an embodiment of the present invention has magnetic resonance (MR) sensitivity due to superparamagnetism of iron oxide, and thus can serve not only as an ultrasonic contrast agent but also be applicable to diagnostic imaging procedures by magnetic resonance (MR).

In addition, according to a specific embodiment of the present invention, the ultrasound contrast agent may further be used for magnetic resonance-guided focused ultrasound (MRgFUS) treatment. In the present invention, the magnetic resonance-guided focused ultrasound treatment is a treatment method using a device that is a combination of a magnetic resonance image (MRI) and ultrasound (ultrasound, US).

This treatment is mainly used to treat fibroids. This treatment method is a non-invasive method that can accurately detect the three-dimensional location of the uterine fibroids through magnetic resonance imaging, and completely ablate the diseased area (myoma tissue) using highly integrated ultrasound, thereby obviating the need for surgical resection.

According to another embodiment of the present invention, the ultrasound contrast agent containing the fine particle of the present invention may also be used as a carrier for drug delivery. The ultrasound contrast agent can be used as a carrier for the delivery of anti-cancer and anti-inflammatory drugs. Cavitation, a unique phenomenon of the ultrasound contrast agent, can temporarily disrupt the tight junction between vascular endothelial cells and thereby facilitate penetration of the drug deeper in the tissues.

Specifically, since the fine particle of the present invention includes hydrophobic bilirubin, it can bind to hydrophobic drugs through hydrophobic interaction. Examples of hydrophobic drugs include, but are not limited to, paclitaxel, docetaxel, and camptothecin-based anti-cancer drugs. It is apparent to those skilled in the art that conventional hydrophobic drugs such as anti-cancer drugs, anti-inflammatory drugs, and anti-inflammatory agents can bind to the fine particle of the present invention without limitation and be delivered.

In addition, the fine particle of the present invention includes bilirubin that forms a coordinate covalent bond with a metal. Therefore, the fine particle of the present invention easily binds to (i) a metal ion or a metal compound such as Cu, Ga, Rb, Zr, Y, Tc, In, Ti, Gd, Mn, Fe, Au, Pt, Zn, Na, K, Mg, Ca, Sr, a lanthanide metal, or (ii) platinum-based anti-cancer drugs such as cisplatin, carboplatin, oxaliplatin, nedaplatin, and heptaplatin.

In the present invention, the coordinate covalent bond formed between (i) the bilirubin derivative and (ii) the metal ion, the metal compound, or the platinum-based anti-cancer drug is formed at the carboxyl group, pyrroling, or lactam group of the bilirubin derivative.

In an embodiment of the present invention, the fine particle of the present invention additionally includes a hydrophobic drug, such as an anthracycline-based anti-cancer drug, taxane-based anti-cancer drug, or camptothecin-based anti-cancer drug. Examples of the anthracycline-based anti-cancer drug in the present invention includes, but are not limited to, daunorubicin, doxorubicin, epirubicin, idarubicin, gemcitabine, mitoxantrone, pirarubicin, and valrubicin, but is not limited thereto.

In addition, examples of the taxane-based anti-cancer drug in the present invention includes, but are not limited to, paclitaxel (paclitaxel), docetaxel (docetaxel) and cabazitaxel.

In addition, since bilirubin composed of the fine particle of the present invention is a natural antioxidant and a reactive oxygen species (ROS)-sensitive substance, it eliminates free radicals from a cancer site or an inflammation site that generates abnormal levels of free radicals. It thus has an anti-inflammatory effect.

The bilirubin derivative contained in the fine particle of the present invention has anti-cancer and angiogenesis-inhibitory effects, as disclosed in Korean Patent Application No. 10-2014-0190881. Therefore, the fine particle of the present invention may be used as a pharmaceutical composition for the treatment of cancer or abnormal angiogenesis.

Examples of inflammatory diseases to which the fine particle of the present invention can be used for treatment include, but are not limited to, inflammatory bowel disease, atopic dermatitis, edema, dermatitis, allergies, asthma, conjunctivitis, periodontitis, rhinitis, otitis media, atherosclerosis, sore throat, tonsillitis, Pneumonia, gastric ulcer, gastritis, Crohn's disease, colitis, hemorrhoids, gout, interstitial spondylitis, rheumatic fever, lupus, fibromyalgia, psoriatic arthritis, osteoarthritis, rheumatoid arthritis, periarthritis, tendinitis, hayitis, myositis, hepatitis, cystitis, Nephritis, Sjogren's syndrome, and multiple sclerosis.

The fine particle of the present invention can also be used for ultrasound thrombolysis (Sonothrombolysis) which treats ischemic disease such as paralysis or myocardial infarction by directly dissolving and treating ultrasound to the thrombus.

Furthermore, since the bilirubin shell removes free radicals, the fine particle can also be applied to prevent ischemic-reperfusion injury, which occurs due to a sudden reperfusion in surrounding ischemic tissues that were acutely or chronically hypoxic. Thus, the fine particle has applicative values distinct from those of conventional ultrasound contrast agents.

The present invention also provides a method of diagnostic imaging of a patient, which includes: (i) administrating an effective amount of the ultrasound contrast agent, containing the fine particle, to a patient, and (ii) imaging a body part or a tissue of the patient.

Another objective of the present invention is to provide a method of diagnostic imaging of a patient, comprising: (i) administrating an effective amount of the ultrasound contrast agent, containing the fine particle, to a patient, and (ii) treating a lesion of a body part or a tissue of the patient. The diagnostic imaging refers to an imaging technique that enhances contrast of an image of a body part or tissue of a patient by using a contrast agent and provides information necessary for diagnosis.

Therapeutic imaging includes a method of treating a patient's disease using a contrast agent having a biological effect in vivo and/or in vitro. Therapeutic imaging is a concept that includes the above-described magnetic resonance-guided focused ultrasound treatment and drug delivery through drug encapsulation.

The term "administration" or "administer" refers to the direct administration of a diagnostically or therapeutically effective amount of the contrast agent (composition) of the present invention to a subject (individual or patient), so that the same amount is formed in the subject's body. The term "therapeutically effective amount" of the composition means a content of the composition sufficient to induce a therapeutic or prophylactic effect on a subject, whom the composition is administered to. The term is also meant to include a "prophylactically effective amount".

The term "diagnostically effective amount" of the composition means a content of the composition sufficient to enhance the contrast effect, to a degree necessary for the diagnosis of a subject, whom the composition is administered to. Also, in the present application, the term "subject" includes, but not limited thereto, humans, mice, rats, guinea pigs, dogs, cats, horses, cows, pigs, monkeys, chimpanzees, baboons, or rhesus monkeys. Preferably, the subject of the present invention is a human.

The diagnostic and the therapeutic imaging methods according to the present invention involve the administration of (i) the fine particle according to the present invention, or (ii) the ultrasound contrast agent containing fine particles. Hereinafter, redundant description thereon is omitted to avoid adding excessive complexity to the specification.

An objective of the present invention is to provide a method for preparing fine particle, including the steps of: (a) dissolving bilirubin derivatives in an aqueous solvent to prepare a bilirubin derivative nanoparticle solution (also referred to as a bilirubin derivative fine particle solution), wherein each of the bilirubin derivatives comprises a bilirubin conjugated with a hydrophilic molecule; and (b) mixing a first organic solution containing a gas with the bilirubin derivative nanoparticle solution and treating the resulting mixture with ultrasound to prepare a fine particle. The fine particle includes a core and a shell. The gas is trapped in the core. The bilirubin derivatives surround the core to form the shell.

The method for preparing the fine particle of the present invention is schematically illustrated in FIG. 1. Hereinafter, a step-by-step method for preparing the fine particle of the present invention is described in detail.

Step (a): a bilirubin derivative nanoparticle solution is prepared by dissolving bilirubin derivative nanoparticles to an aqueous solvent. The bilirubin derivative is a hydrophilic molecule conjugated to bilirubin.

At this step, a hydrophilic or amphiphilic bilirubin derivative is prepared in which bilirubin is conjugated to the hydrophilic molecule. As a result, a nanoparticle solvent containing the bilirubin derivative is prepared. Specifically, the conjugation of the bilirubin to the hydrophilic molecule is achieved by the use of EDC (1-Ethyl-3-(3-dimethylaminopropyl)carbodiimide). This activates the carboxyl group of bilirubin. Then, the bilirubin is bonded to the hydrophilic molecule having an amine group, forming an amide bond. The hydrophilic molecule conjugated to bilirubin has an amine group or is modified to have an amine group.

Specifically, bilirubin is first dissolved in an organic solvent (e.g. dimethyl sulfoxide, DMSO). EDC is added thereto in order to activate the carboxyl group of bilirubin, and reacted at room temperature for 5-30 minutes.

Thereafter, the hydrophilic molecule (e.g. polyethylene glycol), which has an amine group at its terminal, is added and reacted for a predetermined period of time. As a result, a bilirubin derivative bound to the hydrophilic molecule can be synthesized.

Next, the bilirubin derivative, which now has an amide bond formed by the reaction between its carboxyl group and the amine group of the hydrophilic molecule, is separated and purified through a silica column.

The bilirubin derivative prepared as such is dissolved in an organic solvent (e.g. chloroform), and then dried under a nitrogenous atmosphere or in a vacuum to form a film layer.

Thereafter, an aqueous solvent such as a phosphate buffer solution or deionized water is added to the film layer. Then, the resulting solution can be treated with ultrasound to prepare the bilirubin derivative nanoparticle solution.

The bilirubin derivative nanoparticle is a nanoparticle formed by the self-assembly of the bilirubin derivative in an aqueous solvent. The nanoparticles may form a micelle, wherein the hydrophobic bilirubin portions of the nanoparticles are located in the inner region of the bilirubin derivative, while the hydrophilic molecular portions conjugated to bilirubins are exposed to the aqueous solvent.

The method for preparing the nanoparticle solution of bilirubin is conventionally known. In this regard, all contents of Korean Patent Application No. 10-2014-0190881 are incorporated herein by reference in its entirety.

Step (b): a first organic solution containing a gas is mixed with the bilirubin derivative nanoparticle solution. The resulting mixture is treated with ultrasound to prepare a fine particle. The fine particle includes a core and a shell. The gas is trapped in the core. The bilirubin derivatives surround the core to form the shell. In this step, the fine particle is prepared by mixing the hydrophobic gas (e.g. perfluorinated carbon) with the bilirubin derivative nanoparticle solution and encapsulating the hydrophobic gas in the hydrophobic core.

The bilirubin derivative (Pegylated bilirubin) is dissolved in deionized water to obtain the bilirubin nanoparticle solution. The first organic solution containing the hydrophobic gas (e.g. perfluoropentane) is added dropwise to the bilirubin nanoparticle solution, followed by sonication for a predetermined time period. Through the above process, an emulsion-type nano- or micro-bubble system can be prepared. The system includes the hydrophobic gas core surrounded by a shell of the bilirubin derivatives (FIG. 1).

According to another embodiment of the present invention, in the step (b), an organic solution containing metal ions or metal compounds, in addition to the hydrophobic gas, can be added to the bilirubin derivative nanoparticle solution. The metal ions or metal compounds may be selected from the group consisting of Cu, Ga, Rb, Zr, Y, Tc, In, Ti, Gd, Mn, Fe, Au, Pt, Zn, Na, K, Mg, Ca, Sr, and lanthanide metals. The resulting solution can be treated with ultrasound to prepare a fine particle which additionally includes metal ions or metal compounds.

According to yet another embodiment of the present invention, in the step (b), a second organic solution containing the platinum-based anti-cancer drug, in addition to the hydrophobic gas, can be added to the bilirubin derivative nanoparticle solution. The platinum-based anti-cancer drug may be selected from cisplatin, carboplatin, oxaliplatin, nedaplatin, and heptaplatin groups. The resulting solution can be treated with ultrasound to prepare a fine particle which additionally includes a platinum-based anti-cancer drug.

According to yet another embodiment of the present invention, in the step (b), a third organic solution containing anthracycline-, taxane-, or camptothecin-based anti-cancer drug, in addition to the hydrophobic gas, can be added to the bilirubin derivative nanoparticle solution. The platinum-based anti-cancer drug may be selected from cisplatin, carboplatin, oxaliplatin, nedaplatin, and heptaplatin groups. The resulting solution can be treated with ultrasound to prepare a fine particle additionally comprising the anthracycline- or taxane-based anti-cancer drug.

According to yet another embodiment of the present invention, in the step (b), a fourth organic solution containing the superparamagnetic iron oxide nanoparticle (SPION), in addition to the hydrophobic gas, can be added to the bilirubin derivative nanoparticle solution. The resulting solution can be treated with ultrasound to prepare a fine particle additionally comprising the superparamagnetic iron oxide nanoparticle.

The method for preparing the fine particle of the present invention shares the same steps with the method for preparing the fine particle described above. Thus, to avoid adding excessive complexity to the specification, redundant details, such as the type of the gas that comprises the core of the fine particle and the type of the hydrophilic molecule that is conjugated to the bilirubin derivative, is omitted from the specification.

Advantages of Invention

The present invention provides a fine particle, a method for preparing the fine particle, and an ultrasound contrast agent containing the fine particle. The fine particle includes: a core containing a hydrophobic gas therein; and a shell containing a bilirubin derivative and surrounding the surface of the core; And The fine particle containing the bilirubin derivative of the present invention reacts sensitively with reactive oxygen species (ROS) and eliminates free radicals.

In addition, the fine particles of the present invention can be combined with a hydrophobic drug and can effectively chelate metals such as iron oxide nanoparticles.

Therefore, the fine particle of the present invention can be used not only as a ultrasound contrast agent for diagnosis, but also as a magnetic resonance imaging contrast agent, or a carrier for hydrophobic drugs or platinum-based drugs.

EMBODIMENTS

Hereinafter, the present invention will be described in more detail with examples. It is obvious to those skilled in the art that these examples are intended to be more concretely illustrative and the scope of the present invention is not limited to or by the examples

EXAMPLES

Example 1: Preparation of a PEGylated Bilirubin-Based Ultrasound Contrast Agent According to the Present Invention Preparation of Bilirubin Derivative (Pegylated Bilirubin)

The present inventors prepared an amphiphilic derivative of bilirubin in which a hydrophilic molecule was conjugated to bilirubin prior to preparing a bilirubin-based ultrasound contrast agent. Polyethylene glycol was used as the hydrophilic molecule.

Specifically, bilirubin was first dissolved in dimethylsulfoxide (DMSO), and an appropriate amount of EDC (1-Ethyl-3-(3-dimethylaminopropyl)carbodiimide) was added to activate the carboxyl group present in bilirubin, so as to induce the desired reaction. The solution was then reacted at room temperature for about 10 minutes.

Next, polyethylene glycol, which has an amine group at its terminal, was added. The resulting solution is laid for reaction for a certain time period. The carboxyl group of bilirubin was covalently bonded to the amine group of polyethylene glycol via the formation of amide bonds, thereby forming the bilirubin derivative.

Finally, the bilirubin derivative prepared from the above method was purified and extracted using a silica column.

Preparation of Ultrasonic Contrast Agent Coated with Pegylated Bilirubin

A bilirubin-based echogenic nanoparticle (or microparticle) of the present invention was prepared by a simple oil-in-water (O/W) emulsification method. A bilirubin nanoparticle particle solution (1.2 mg/2 ml) was prepared by dissolving the bilirubin derivative (Pegylated bilirubin) prepared in Example 1-1 in deionized water, and transferring the resulting solution to an ice bath equipped with a probe type ultrasonic grinder.

Figure 1:
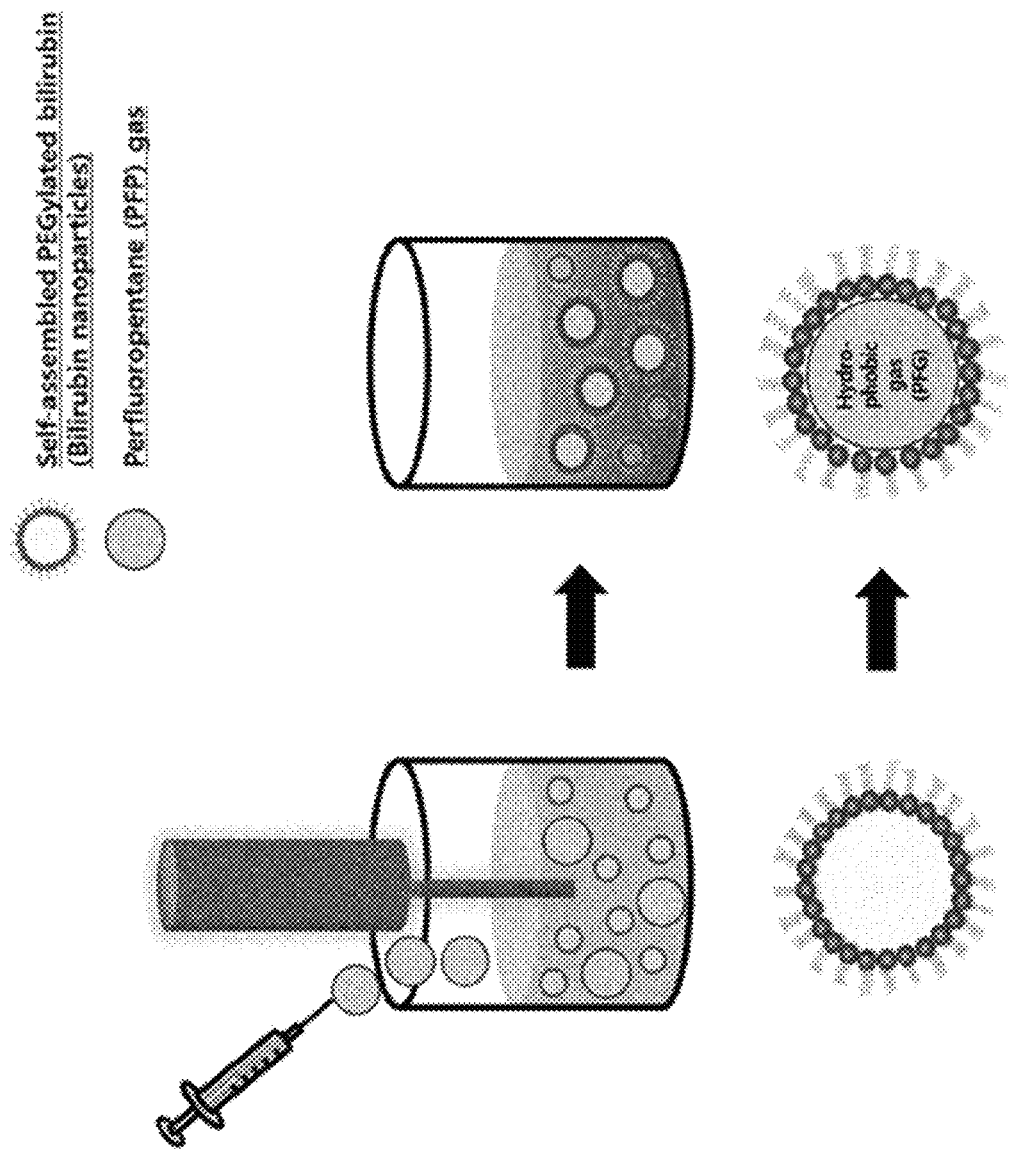
FIG. 1 is a diagram schematically illustrating a method of preparing an ultrasonic contrast agent coated with a pegylated bilirubin according to the present invention.
Figure 2:
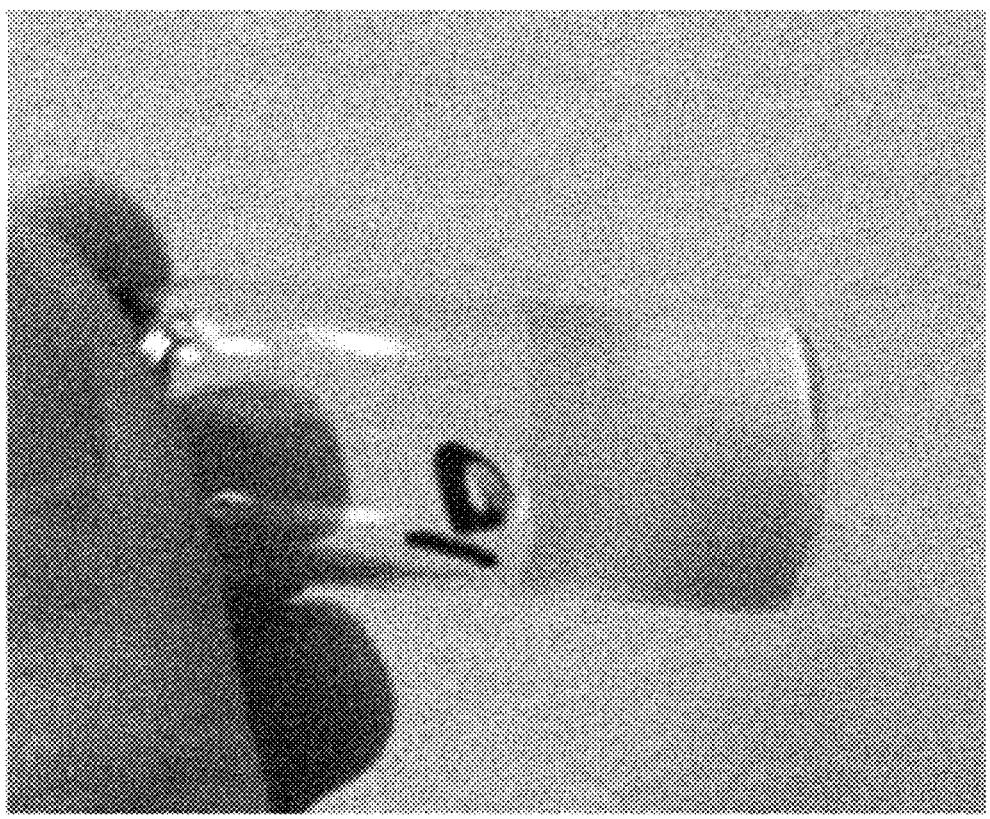
FIG. 2 is a photograph of the ultrasonic contrast agent coated with the pegylated bilirubin according to the present invention.

Perfluoropentane (PFP) was used as a hydrophobic gas forming a bubble core. Perfluoropentane (organic phase) is added dropwise to the bilirubin nanoparticle particle solution (aqueous phase) at various volume ratios (PFP, 2.5, 5, 10% v/v). The resulting solution was treated with ultrasound at a power of 30% for 90 seconds. As a result, an emulsion type of nano- or micro-bubble system was prepared. The system has a core composed of hydrophobic gas (perfluoropentane) and a shell composed of bilirubin derivatives (FIGS. 1 and 2).

Example 2: Phantom Imaging of the PEGylated Bilirubin-Based Ultrasound Contrast Agent According to the Present Invention The ultrasound phantom image was obtained using an ultrasound device probe, Vevo770. The Vevo770 (High-Resolution Micro-Imaging System, Visualsonics, Toronto, Canada) is equipped with an RMV 706 probe. The present inventors used agar-gel phantoms prepared by embedding 500 µL of Eppendorf tubes in a 3% (w/v) agarose gel to simulate in vivo conditions for ultrasound imaging.

First, the PEGylated bilirubin-based contrast agent samples of the present invention, each with a unique volume ratio of perfluoropentane (PFP) in the hydrophobic gas core (PFP 0, 2.5, 5, 10% v/v), was placed in agar gel phantom. The images were obtained by treating each sample with 40 MHz ultrasound.

The change in the ultrasonic intensity of each sample (PFP 0, 2.5, 5, 10% v/v) was measured for 180 minutes. The measured change was normalized by subtracting the ultrasonic intensity of the water control from the sample's ultrasonic intensity. The echogenic characteristics of each sample of the PEGylated bilirubin solution, with different volume ratios of PFP in the gas core, were hourly monitored. The results are shown in FIGS. 3-5.

Figure 3:
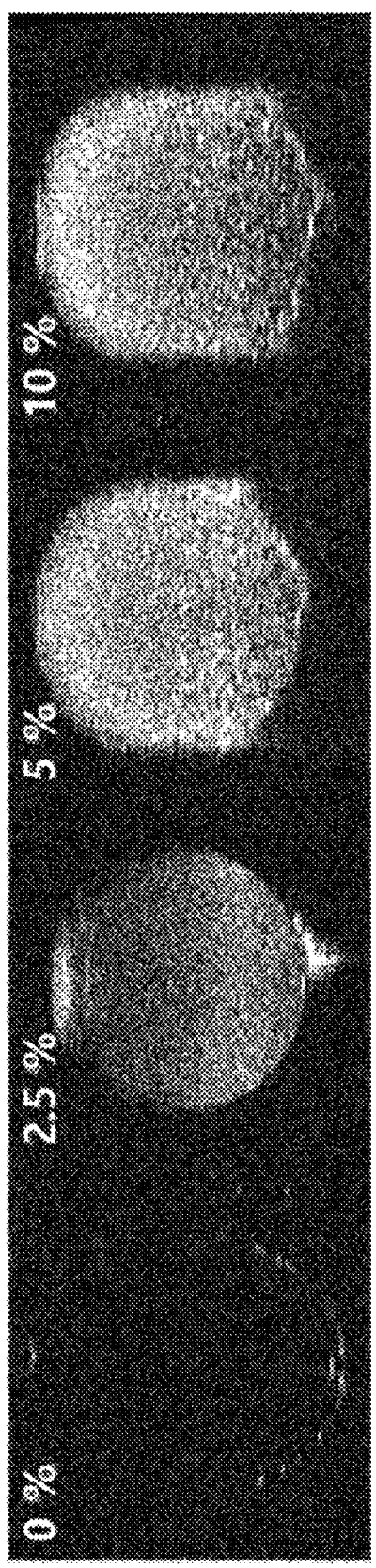
FIG. 3 shows representative phantom images of the ultrasonic contrast agent samples at the beginning of the measurement (t=0 min). Each of the ultrasonic contrast agent samples is coated with pegylated bilirubin. The samples had different volume ratios of perfluoropentane (PFP) in the hydrophobic gas core (PFP 0, 2.5, 5, 10% v/v).

FIG. 3 shows representative phantom images of the ultrasound contrast agent samples at the beginning of the measurement (t=0 min). Each of the ultrasonic contrast agent samples is coated with pegylated bilirubin. The samples had different volume ratios of perfluoropentane (PFP) in the hydrophobic gas core (PFP 0, 2.5, 5, 10% v/v).

Figure 4:
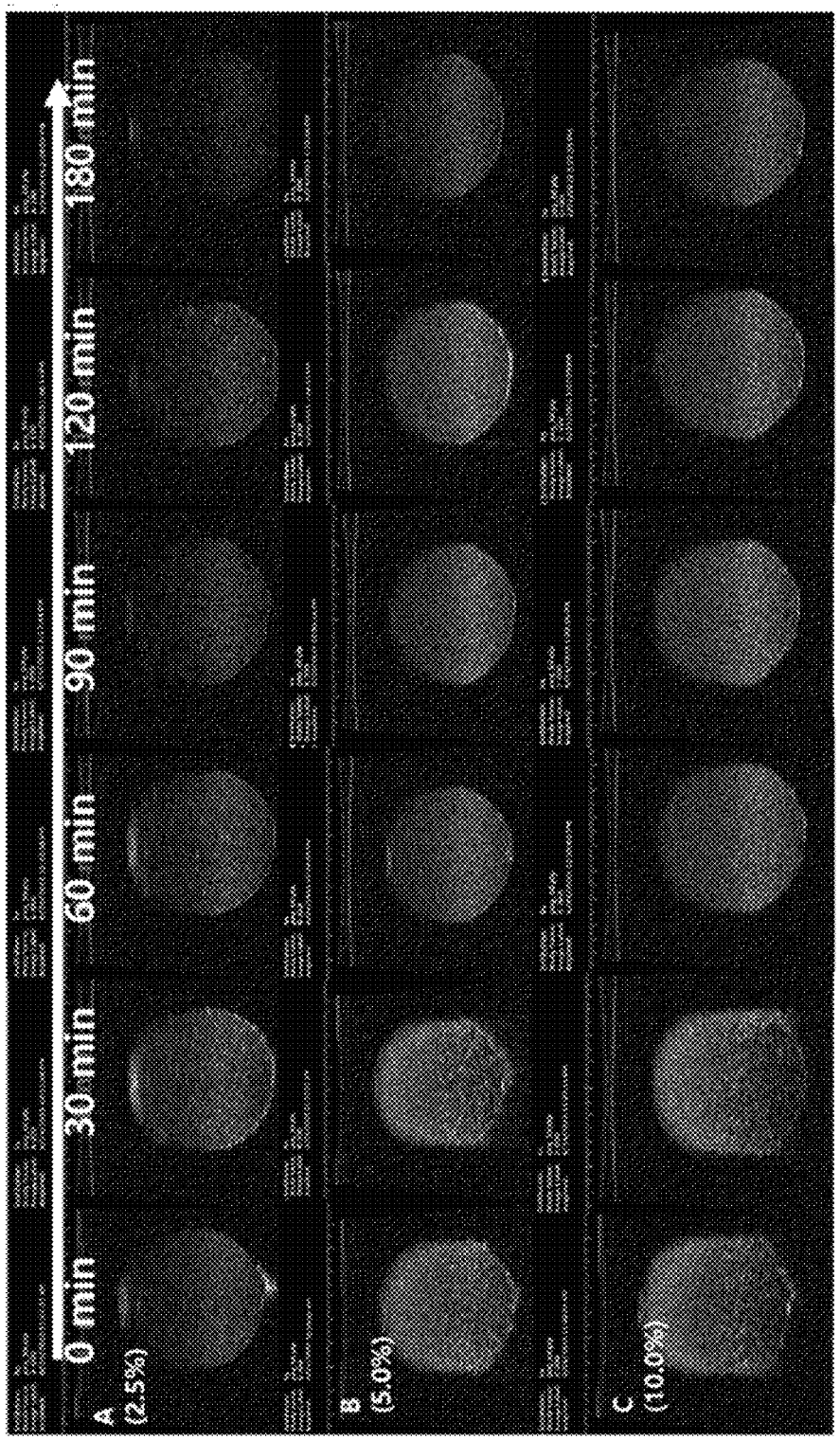
FIG. 4 is a graph showing hourly changes in phantom images of the ultrasonic contrast agent samples which are coated with pegylated bilirubin. The samples had different volume ratios of perfluoropentane (PFP) from each other in the hydrophobic gas core (PFP 0, 2.5, 5, 10% v/v).

FIG. 4 is a graph showing hourly changes in phantom images of the samples of the contrast agent coated with pegylated bilirubin, each with a unique volume ratio of perfluoropentane (PFP) in the hydrophobic gas core (PFP 0, 2.5, 5, 10% v/v). As shown in FIGS. 3-4, the highest level echogenicity was observed in the PFP 5.0% (v/v) experimental group.

Figure 5:
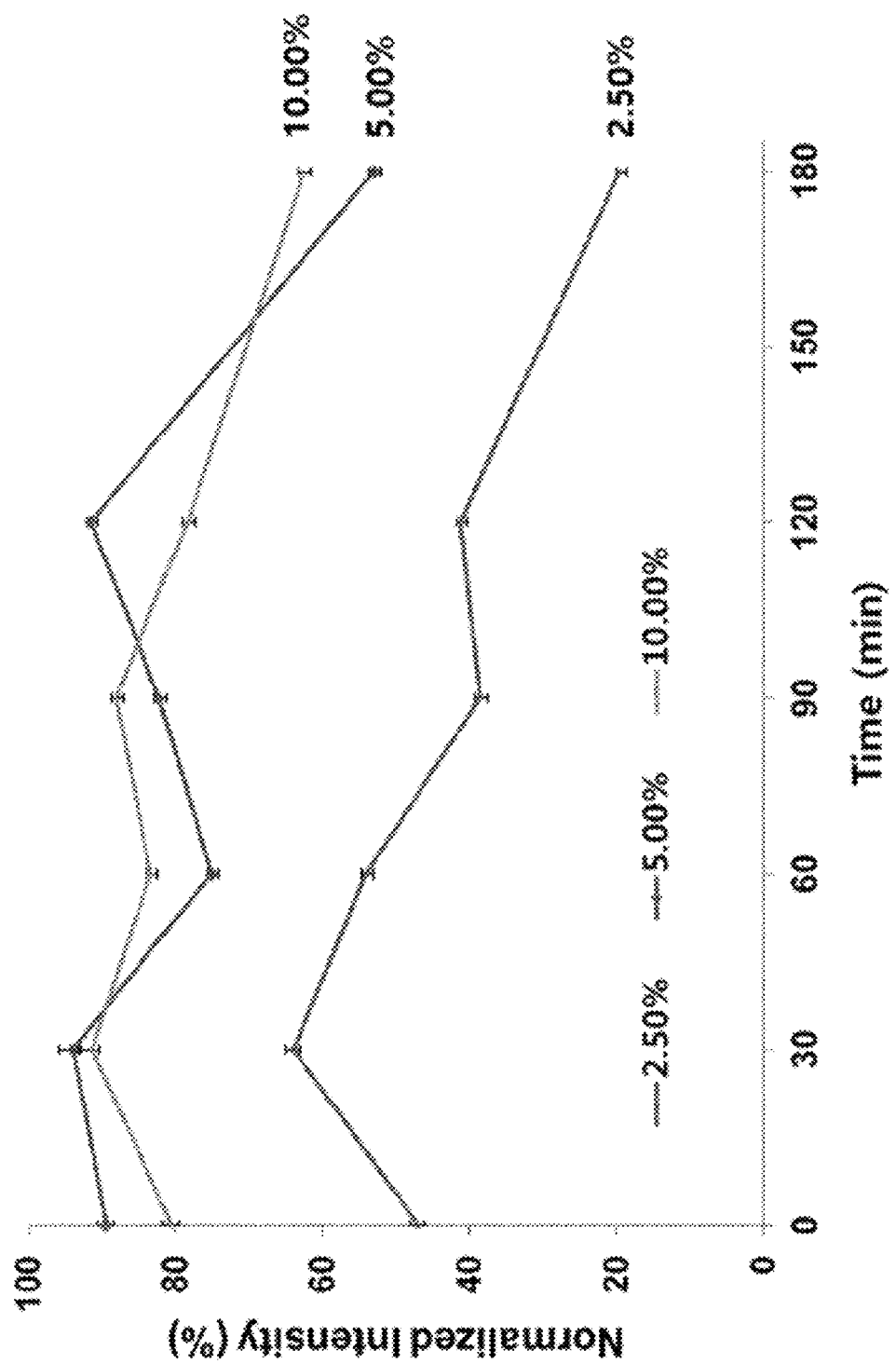
FIG. 5 is a graph showing normalized ultrasound intensity of the phantom images of the ultrasonic contrast agent samples which are coated with pegylated bilirubin over time. The samples had different volume ratios of perfluoropentane (PFP) from each other in the hydrophobic gas core (PFP 0, 2.5, 5, 10% v/v).

FIG. 5 is a graph showing normalized ultrasound intensity of the phantom images of the ultrasonic contrast agent samples which are coated with pegylated bilirubin over time. The samples had different volume ratios of perfluoropentane (PFP) from each other in the hydrophobic gas core (PFP 0, 2.5, 5, 10% v/v). The in-situ half-life of the echo signal of the PEGylated bilirubin-based ultrasound contrast agent was about 45 minutes.

From the above results, it was confirmed that the bilirubin derivative of the present invention, which is formed by the conjugation of the hydrophilic molecule to the PEGylated bilirubin, functions as a stable shell surrounding the hydrophobic gas core. The phantom imaging also confirmed the enhancement effect on ultrasonic imaging. Therefore, the bilirubin derivative-based fine bubbles prepared according to the present invention can be useful as an ultrasound contrast agent.

Figure 6:
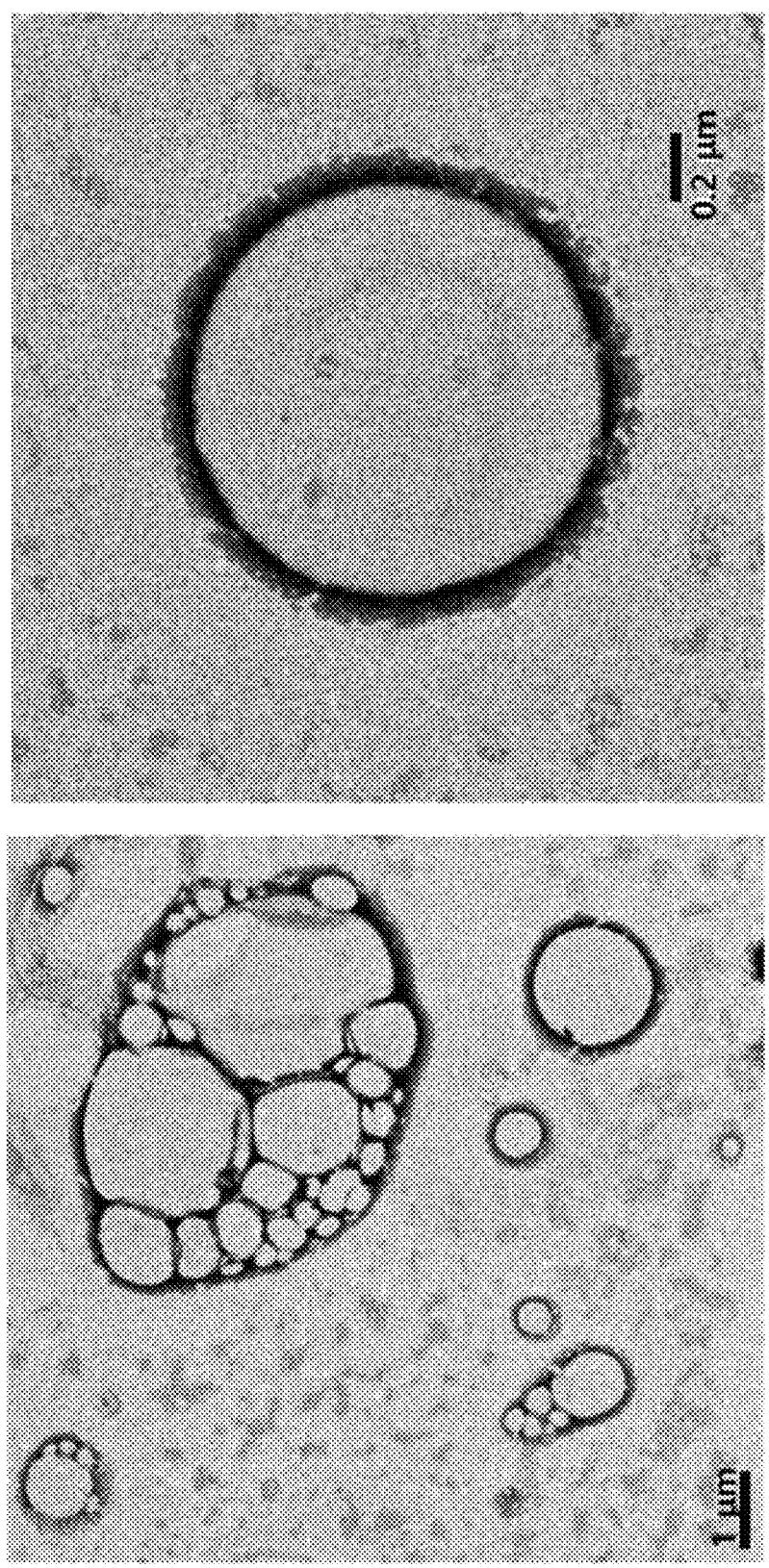
FIG. 6 shows transmission electron microscope images of the ultrasonic contrast agent which is coated with pegylated bilirubin. The measured size of the contrast agent bubble was 2-4 μm.
Figure 7B:
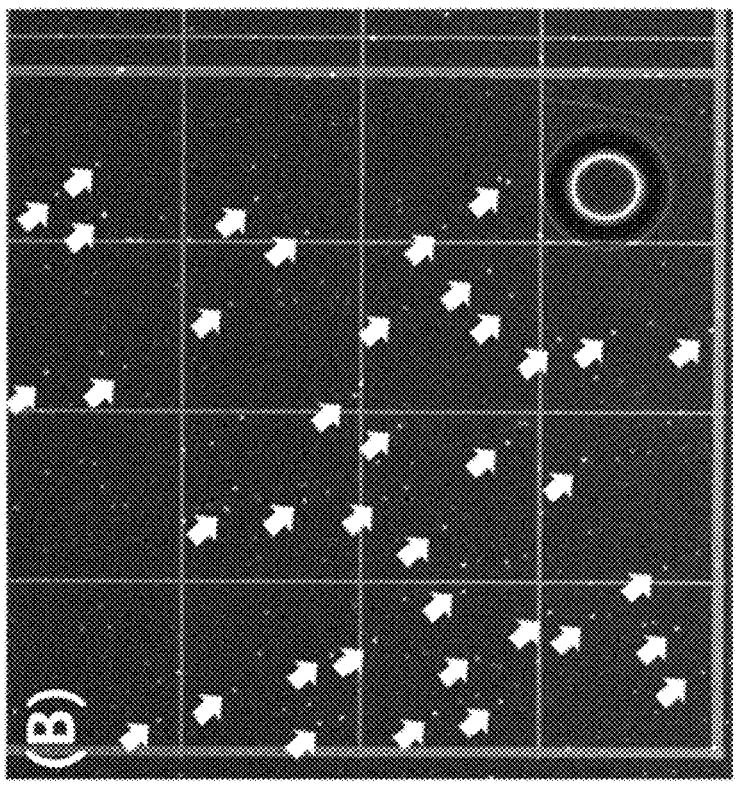
FIG. 7B is an image showing the ultrasound contrast agent dispensed on a hemocytometer grid. This image allowed the determination of the number of the contrast agent per volume.
Figure 7A:
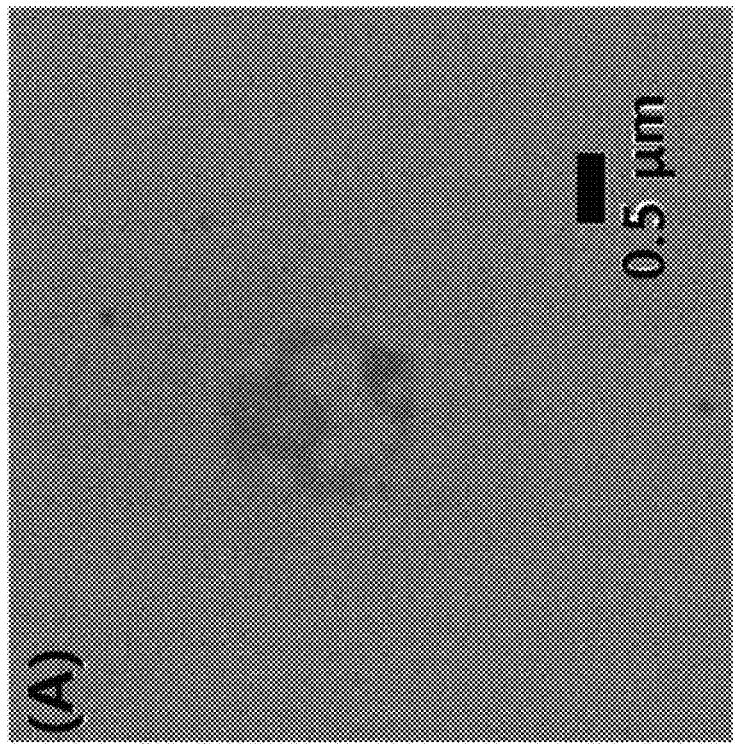
FIG. 7A is an image showing the ultrasonic contrast agent (white arrows) under an optical microscope. The ultrasonic contrast agent is coated with pegylated bilirubin.

Example 3: Features of the Pegylated Bilirubin-Based Ultrasound Contrast Agent According to the Present Invention 3-1. Microscope Morphology Microscopic morphology of the fine particle was observed with a negative staining of uranium acetate, a transmission electron microscope (Tecnai G2 F30, Eindhoven, Netherlands) (FIG. 6), and an optical microscope under cover slip (FIGS. 7A and 7B). FIG. 6 shows the PEGylated bilirubin-based ultrasound contrast agent of the present invention observed by transmission electron microscopy (TEM). FIG. 6 shows micro-sized bubble particles constituting the ultrasound contrast agent of the present invention.

FIG. 7A shows the PEGylated bilirubin-based ultrasound contrast agent of the present invention observed with an optical microscope. In order to determine the number of bubbles contained per volume of contrast agent, the PEGylated bilirubin-based contrast agent of the present invention was placed on a hemocytometer grid and the bubbles were counted (FIG. 7B). It was confirmed that about $2.0 \times 10^9$ bubbles were contained per ml of the contrast agent of the present invention.

3-2. Pegylated Bilirubin-Based Ultrasound Contrast Agent Activity on Reactive Oxygen Species (ROS)

Figure 8:
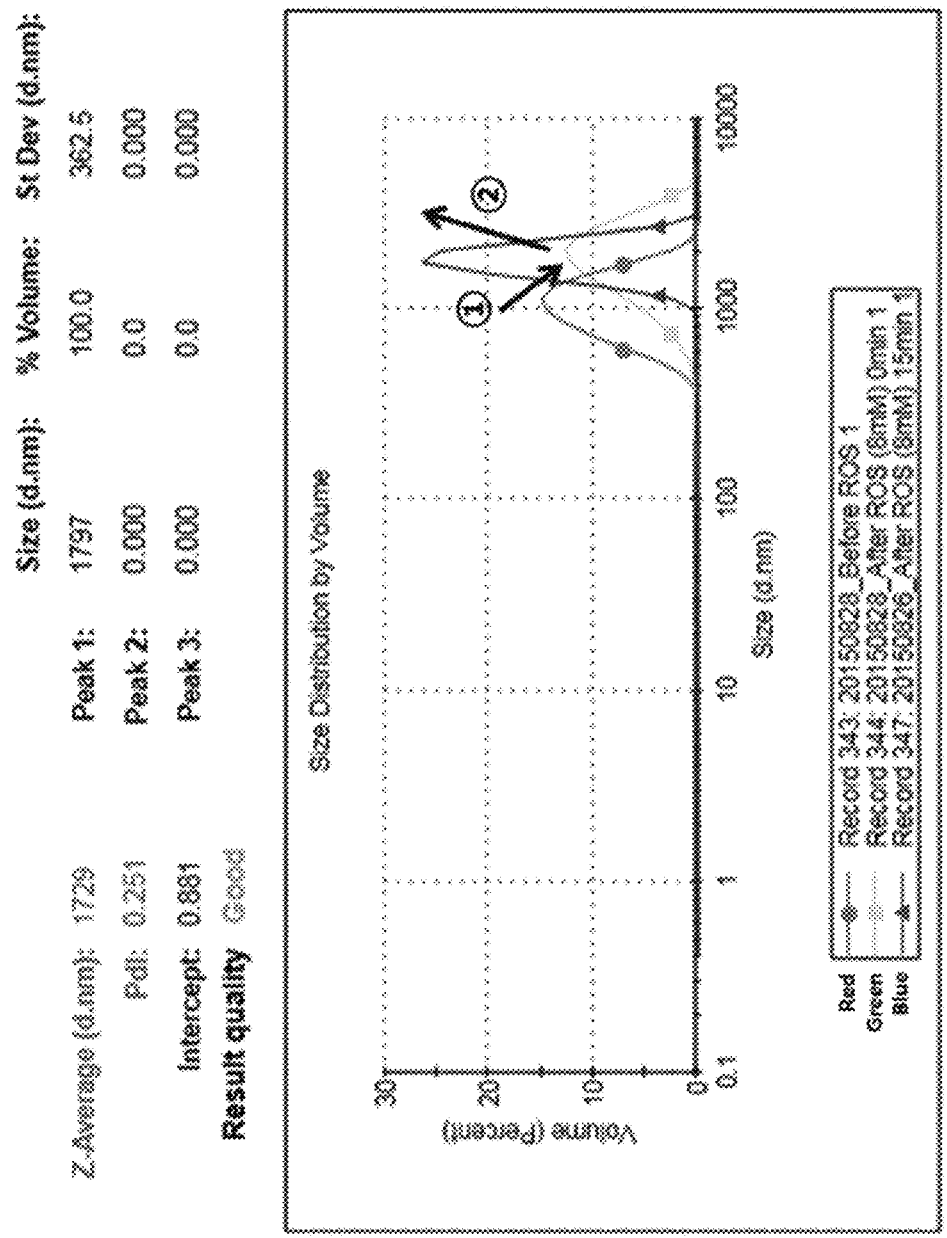
FIG. 8 is a graph showing a gradual increase [red(●), ①green(■)→②blue(▲)] in hydrodynamic size of the ultrasonic contrast agent after treatment with reactive oxygen species. The ultrasonic contrast agent is coated with pegylated bilirubin.

The PEGylated bilirubin-based ultrasound contrast agent of the present invention includes bilirubin, which is a natural antioxidant. The present inventors used the Nanosizer ZS 90 (Malvern Instruments, Ltd., Malvern, UK) to confirm the reactivity of the ultrasonic contrast agent of the present invention to reactive oxygen species (ROS). The hydrodynamic size distribution of the microbubble of the contrast agent of the present invention before/after treatment with reactive oxygen species (ROS, $H_2O_2$) was measured. The results are shown in FIG. 8. As shown in FIG. 8, the hydrodynamic size of the bubble increased as the ultrasonic contrast agent of the present invention reacted with reactive oxygen species ($H_2O_2$).

Bilirubin is a natural antioxidant in the body. When bilirubin reacts with the reactive oxygen species, which is rich in a diseased site, bilirubin is converted to biliverdin. As a result, the hydrophobic interaction between the bilirubin derivatives and the gas core is weakened, and the amphiphilic bilirubin derivative-coated shell of the contrast agent bubble is destroyed. Eventually, the instantaneous conglomeration of the hydrophobic gas core occurs. Then, the contrast of the ultrasound image is enhanced by a degree proportional to the gradual increase in size of the bubble (FIG. 8).

Accordingly, the bilirubin derivatives, including the PEGylated bilirubin combined with a hydrophilic molecule, can enhance the ultrasound image of diseased sites in which the reactive oxygen species are rich. They also exhibit an antioxidant effect in the diseased sites due to their inherent antioxidant properties. Therefore, the fine particle containing the bilirubin derivative of the present invention can be useful not only for diagnosis based on ultrasound examinations but also for treatment of diseases.

Example 4: Preparation of PEGylated Bilirubin-Based Ultrasonic Contrast Agent Loaded with Iron Oxide Nanoparticle Loading of iron oxide nanoparticles was performed by modifying the method for preparation described above in Example 1. When making an oil-in-water (O/W) layer, a solution of iron oxide nanoparticles dispersed in hexane was added to the perfluoropentane (PFP) organic phase.

Then, ultrasound treatment is performed to obtain an emulsion, as described above. The emulsion was agitated under dim light for 6 hours to evaporate hexane. Then, it was centrifuged at 5000 rpm and aggregates were removed. The supernatant was isolated and iron oxide nanoparticle-loaded PEGylated bilirubin microbubble was extracted using a rare earth magnet (FIG. 9 and FIGS. 10A and 10B).

Figure 9:
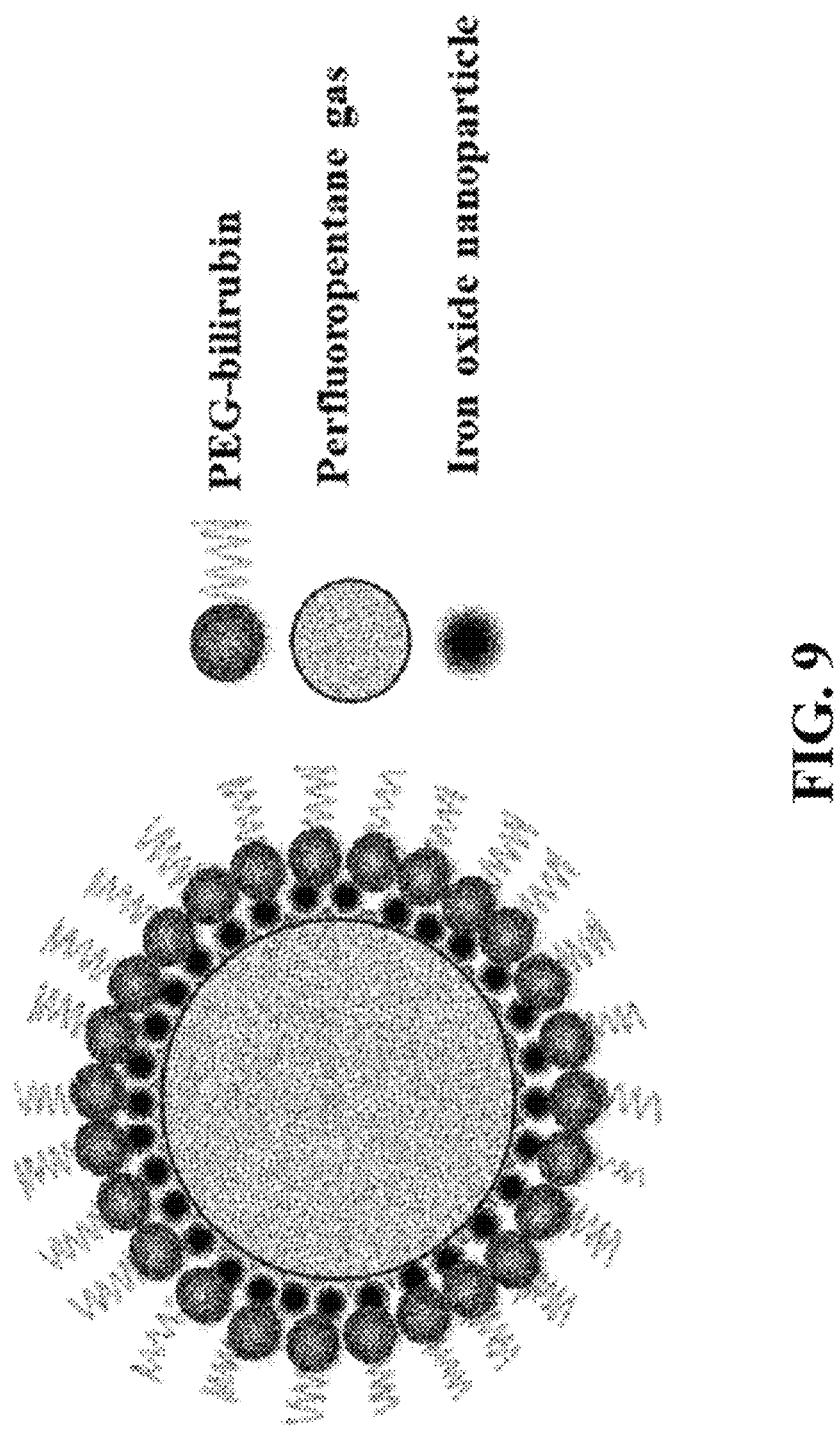
FIG. 9 is a diagram schematically illustrating the ultrasonic contrast agent coated with PEGylated bilirubin and loaded with iron oxide nanoparticle.
Figure 10B:
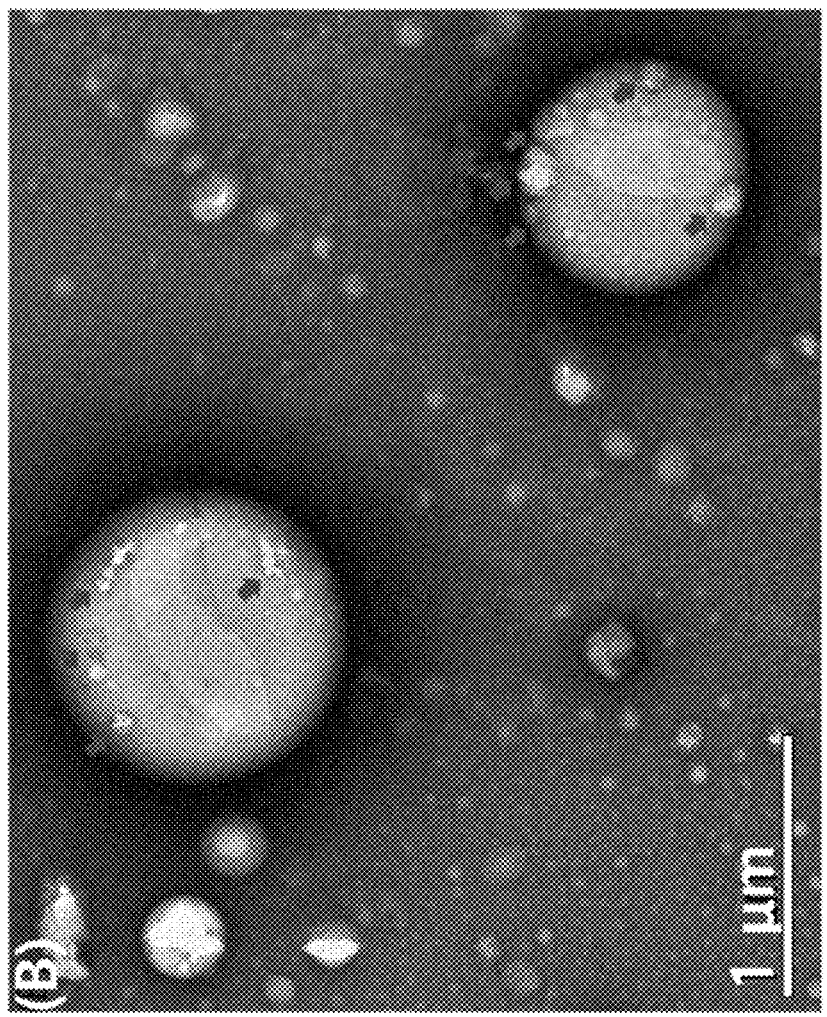
FIG. 10B is a transmission electron microscopic image of iron oxide nanoparticle-loaded PEGylated bilirubin coated US contrast agents.

FIG. 9 is a diagram schematically illustrating the iron oxide nanoparticle-loaded PEGylated bilirubin-based, prepared according to the method described above. As shown in FIG. 9, in the ultrasonic contrast agent of the present invention, the hydrophobic region (hydrophilic molecule) of the bilirubin-hydrophilic polymer conjugate is exposed to the aqueous phase. The hydrophobic region (bilirubin) of the bilirubin-hydrophilic polymer conjugate is in direct contact with the hydrophobic gas (PFP) core.

Here, bilirubin can bind to the iron oxide nanoparticle as follows. The oleic acid layer, coated on the iron oxide nanoparticle, falls off. Then, the carboxyl group of bilirubin binds to the iron oxide nanoparticle through a chelation reaction. Alternatively, when the core has a relatively large volume, 15 nm-sized iron oxide nanoparticles may be loaded onto the hydrophobic gas core via hydrophobic interaction.

Figure 10A:
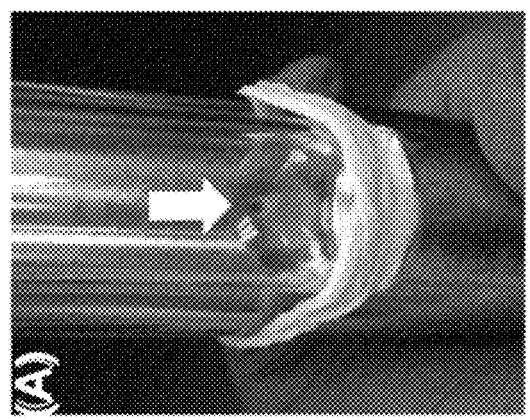
FIG. 10A is an image showing a position (arrow) in which PEGylated bilirubin loaded with iron oxide nanoparticles is attached to a magnet.

FIG. 10A shows that, when the PEGylated bilirubin contrast agent loaded with iron oxide nanoparticle is extracted with a magnet, the contrast agent containing iron oxide nanoparticle is attracted to the magnet (red arrow). FIG. 10B shows a transmission electron microscope image of an ultrasonic contrast agent coated with PEGylated bilirubin loaded with iron oxide nanoparticle. The arrows in FIG. 108 point to the iron oxide nanoparticle loaded on the microbubble of the PEGylated bilirubin-based ultrasound contrast agent according to the present invention. The size of the iron oxide nanoparticle is about 15 nm.

The above results confirmed that magnetic resonance sensitive metal particles, including iron oxide nanoparticles, can be loaded to the ultrasonic contrast agent according to the present invention. The ultrasonic contrast agent includes the bilirubin derivative conjugated to the hydrophilic molecule. Therefore, the bilirubin derivative-based ultrasound contrast agent of the present invention can be used not only as an ultrasound contrast agent, but also as a contrast agent for MR-guided focused ultrasound (MRgFUS).

Furthermore, the chelating properties of the metal particles of bilirubin are used to load a platinum-based anti-cancer drug, rather than iron oxide nanoparticle, on the ultrasonic contrast agent of the present invention. In this case, the contrast agent can also serve as a carrier for anti-cancer drug delivery. The magnetic resonance-guided focused ultrasound (MRgFUS) is a novel technique that can temporarily increase the permeability of the blood-brain barrier (BBB).

The use of magnetic resonance-guided focused ultrasound enables the delivery of therapeutic agents into the central nervous system and increases the efficiency of the treatment of brain tumors. Therefore, the ultrasound contrast system of the present invention can be a useful platform technology capable of simultaneously performing three roles: an ultrasound contrast agent, a magnetic resonance sensitive contrast agent, and an antioxidant/anti-cancer delivery carrier.

What is claimed is:

1. A fine particle, comprising:
   a core containing a gas; and
   a shell comprising a bilirubin derivative and surrounding the corer, wherein the bilirubin derivative is a bilirubin conjugated with a hydrophilic molecule, and the bilirubin is closer to the core than the hydrophilic molecule.

2. The fine particle of claim 1,
   wherein the gas is selected from the group consisting of air, nitrogen, helium, argon, carbon dioxide, sulfur hexafluoride ($SF_6$), and $C_1$ to $C_{10}$ perfluorocarbons.

3. The fine particle of claim 1,
   wherein the hydrophilic molecule is selected from the group consisting of dextran, carbodextran, polysaccharide, cyclodextran, pluronic, cellulose, starch, glycogen, carbohydrate, monosaccharide, disaccharide and oligosaccharide, polypeptide, polyphosphazene, polyethylene glycol, PEG, Methoxy polyethylene glycol (methoxy polyethylene glycol, mPEG), polypropylene glycol, polyethylenimine, poly-L-lysine, polyglycolide, polymethyl methacrylate, Polyvinylpyrrolidone, poly(acrylate), poly(acrylamide), poly(vinylester), poly(vinyl alcohol) (poly[vinyl alcohol]), polystyrene, polyoxide, polyelectrolyte, poly(N-vinylpyrrolidone), poly(N-vinyl pyrrolidone), polyvinylamine, poly(beta-hydroxyethyl methacrylate), polyethylene oxide, poly(ethylene oxide-b-propylene oxide), and polylysine.

4. The fine particle of claim 1, further comprising:
   a metal ion or a metal compound selected from the group consisting of Cu, Ga, Rb, Zr, Y, Tc, In, Ti, Gd, Mn, Fe, Au, Pt, Zn, Na, K, Mg, Ca, Sr, and lanthanide metals.

5. The fine particle of claim 1, further comprising:
   an anti-cancer drug loaded in the core,
   wherein the anti-cancer drug is selected from the group consisting of a platinum-based anti-cancer drug, an anthracycline-based anti-cancer drug, a taxane-based anti-cancer drug, and a camptothecin-based anti-cancer drug,
   wherein the platinum-based anti-cancer drug is selected from the group consisting of cisplatin, carboplatin, oxaliplatin, nedaplatin, and heptaplatin,
   wherein the anthracycline-based anti-cancer drug is selected from the group consisting of daunorubicin, doxorubicin, epirubicin, idarubicin, gemcitabine, mitoxantrone, pirarubicin, and valrubicin,
   wherein the taxane-based anti-cancer drug is selected from the group consisting of paclitaxel, docetaxel, and cabazitaxel.

6. The fine particle of claim 1, further comprising:
   a superparamagnetic iron oxide nanoparticle (SPION) which is loaded in the core.

7. An ultrasound contrast agent comprising:
   a core containing a gas; and
   a shell comprising a bilirubin derivative and surrounding the core,
   wherein the bilirubin derivative is a bilirubin conjugated with a hydrophilic molecule, and the bilirubin is closer to the core than the hydrophilic molecule.

8. The ultrasound contrast agent of claim 7, further comprising:
   a drug,
   wherein the ultrasound contrast agent serves as a drug delivery system.

9. A method for obtaining a diagnostic image by magnetic resonance (MR), comprising:
   administrating an effective amount of an ultrasound contrast agent to a subject, wherein the ultrasound contrast agent includes the particle of claim 1; and imaging a body part or a tissue of the subject by magnetic resonance (MR).

10. The method of claim 9,
wherein the magnetic resonance (MR) is MR-guided focused ultrasound (MRgFUS).

\* \* \* \* \*